United States Patent [19]

Hsu et al.

[11] Patent Number: 5,243,865

[45] Date of Patent: Sep. 14, 1993

[54] DERMAL EXPOSURE TESTING METHOD AND APPARATUS THEREFOR

[75] Inventors: Jong-Ryng Hsu; David E. Camann; Kevin Villalobos, all of San Antonio, Tex.

[73] Assignee: Southwest Research Institute, San Antonio, Tex.

[21] Appl. No.: 955,922

[22] Filed: Oct. 2, 1992

Related U.S. Application Data

[62] Division of Ser. No. 694,319, May 1, 1991, abandoned.

[51] Int. Cl.⁵ .................. G01N 1/02; G01N 33/00
[52] U.S. Cl. .................. 73/864.72; 73/864.71
[58] Field of Search ............ 73/864.72, 864.71, 865.7, 73/866.4; 128/743; 436/2, 8

[56] References Cited

U.S. PATENT DOCUMENTS

| | | | |
|---|---|---|---|
| 3,091,967 | 6/1963 | Hardlow et al. | 73/864.71 |
| 3,393,114 | 7/1968 | Jorgensen | 156/523 |
| 3,430,496 | 3/1969 | Swanberg et al. | 73/864.71 |
| 3,463,694 | 8/1969 | De Roshia | 156/523 |
| 4,103,553 | 8/1978 | De Blasiis et al. | 73/864.71 |
| 4,487,788 | 12/1984 | Scheie et al. | 73/864.72 X |
| 4,848,165 | 7/1989 | Bartilson et al. | 73/864.71 |
| 4,848,167 | 7/1989 | Gordon et al. | 73/864.71 |
| 5,060,527 | 10/1991 | Burgess | 73/865.7 X |

Primary Examiner—Tom Noland

[57] ABSTRACT

Propellable apparatus for use in sampling for the contact transfer of a chemical residue on a surface comprising a frame having shoulders with movable supports at one end thereof and having mounted on the other end a roller having thereon a cylindrical layer of a resilient material with chemical residue contact transfer absorption properties similar to human skin, the roller being pivotably mounted such that a desired constant pressure, based on the weight of the roller, is maintained regardless of pressure applied to the shoulder to propel the apparatus.

3 Claims, 1 Drawing Sheet

DERMAL EXPOSURE TESTING METHOD AND APPARATUS THEREFOR

This application is a division of application Ser. No. 07/694,319 filed May 1, 1991 and now abandoned.

BACKGROUND OF THE INVENTION

The present invention relates to a method for testing for chemical residue on a surface and apparatus suitable therefor. It is particularly intended to simulate dermal exposure of a young child to chemical residues, particularly pesticides.

In many environments, particularly in home environments, young children who tend to crawl on hands and knees or even to walk barefoot on floors or slide on their stomachs thereon are exposed to chemical residues on such indoor surfaces and in house dust and it is desired to determine the levels of such exposure. There is at present no method or apparatus that will reliably reflect the exposure of young children to such chemical residues on indoor surfaces. In particular, there are no means whereby the instrument sampling the surface have similar pesticide or chemical contact transfer efficiency as the human skin and that the instrument be capable of applying to the surface to be sampled the same pressure or similar one to which a young child will exert when it is either crawling, walking or sliding as on its stomach on such surface.

Further, there are no accurate means to enable one to ensure that contact transfers can be accurately and readily measured. It is, of course, also often necessary to determine the dermal exposure of adults to such residues.

SUMMARY OF THE INVENTION

The present invention provides a simple procedure for accurately determining dermal exposure to the chemical residues, particularly pesticide residues on indoor surfaces, and an apparatus for accurately sampling the same.

Briefly, the present invention comprises the method of testing for contact transfer of a chemical residue on a surface possibly exposed to the same so as to simulate the contact transfer of a human skin from dermal exposure to said chemical residue by coming into dermal contact with said surface, comprising applying a layer of a material having chemical residue contact transfer and sorption properties similar to that of human skin to said surface at a substantially constant pressure, subjecting the thus applied layer to extraction with a liquid extractor to extract therefrom any said chemical residue if present in or on said layer, and testing the resultant extractant by means suitable to determine whether any said chemical residue is present in said extractant.

The invention also comprises the apparatus for sampling the contact transfer of such residue as hereinafter described.

DETAILED DESCRIPTION

Figure 1:
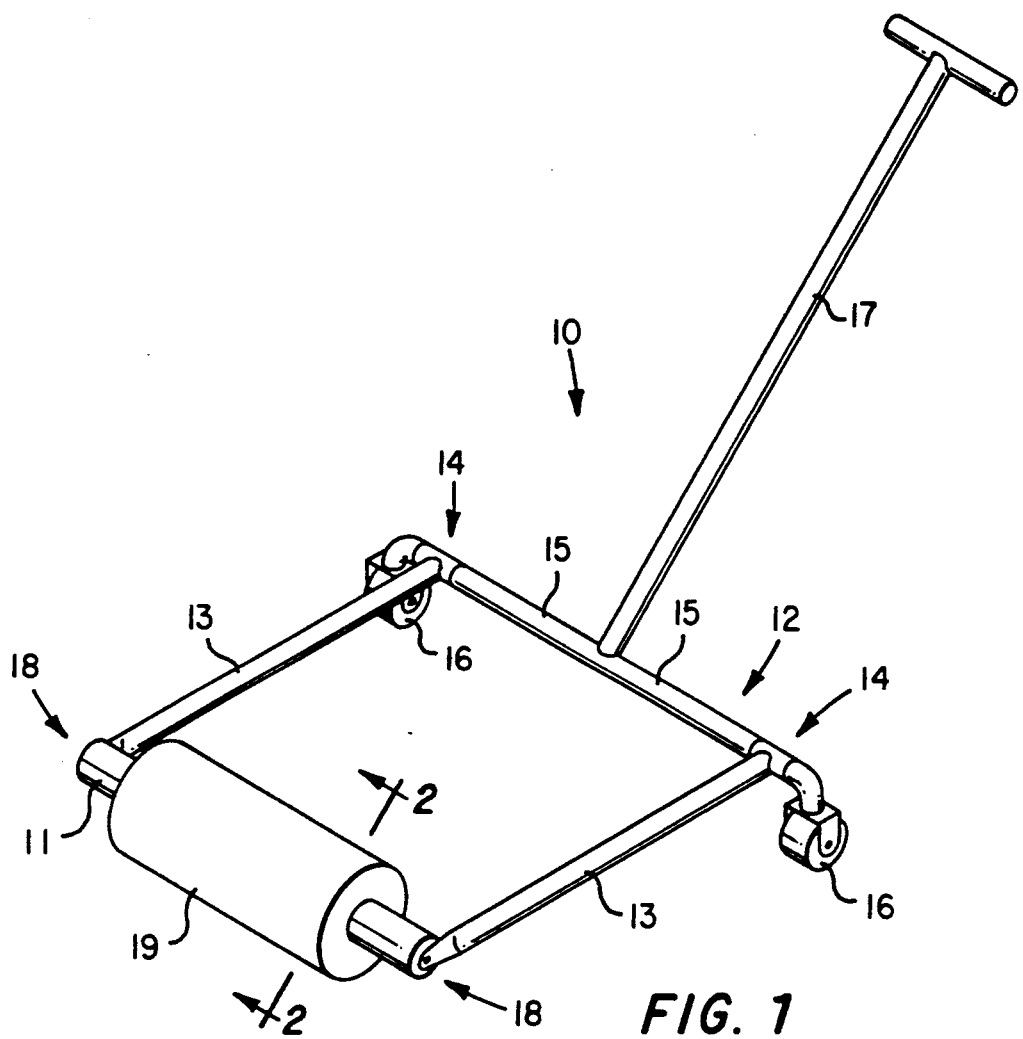
FIG. 1 is a perspective view of apparatus in accord with the instant invention and FIG. 2 is a sectional view taken along line 2—2 of FIG. 1.
Figure 2:
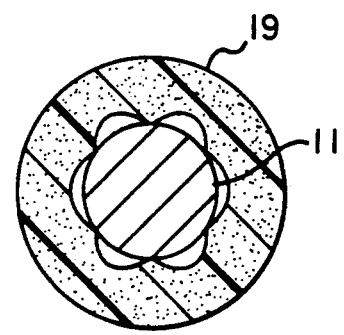

Referring first to the apparatus of the instant invention, there is depicted in FIGS. 1 and 2 a preferred embodiment thereof. It comprises a sampling apparatus 10 having roller means 11, preferably a stainless steel cylinder, rotatably mounted on frame means 12. Such frame means 12 can be suitably any tubular plastic or metal as can the leg means 13. Legs 13 of the frame means are pivotably mounted at one end at points 14 on shoulder means 15 and at the other end 18 have roller means 11 screwed thereon. By pivotably mounting legs 13 to shoulder means 15, a constant pressure based on the weight of roller means is applied to the sampled surface regardless of pressure applied to shoulder means 15. Shoulder means 15 are mounted to movable supports 16, preferably casters, to make the device more readily movable and in a uniform manner on a surface and to absorb pressure applied to shoulder means 15. Attached approximately midway to the shoulder portions of the frame means are propelling means 17 preferably just a wood, metal or plastic tube of a length sufficient for an adult to hold on to the same and propel the device.

Removably mounted on the roller 11 is a cylindrical material 19 having chemical residue contact transfer and sorption properties similar to that of human skin. Preferably, the material is a polyurethane foam. The polyurethane foam layer 19 may be covered with a layer of nylon, filter paper, cloth, or other covering material. In that case, only the cover may be extracted, as discussed below, for the compound of interest.

The polyurethane foam is preferred since it has a chemical residue, particularly pesticide contact transfer, efficiency extremely similar to that of the human skin.

This cylindrical-foam layer 19 is readily applied and removed from the roller means simply by unscrewing the roller 11 from one or both legs 13, then sliding the cylindrical layer 19 from the roller means 11. If desired, of the cylindrical foam layer can be moistened or a sheet of a material such as Teflon ® can be inserted on its interior surface to make it more readily removable and insertable on the roller means 11. This is particularly true since the inner dimensions of the opening in the cylinder must be of a size such that they will snuggly engage the exterior surface means so that when the device is used and pressure is placed on the roller means and the cylinder foam layer thereon the device will roll to permit the entire exterior cylindrical surface to come in contact with the indoor surface such as the floor being tested for chemical residue.

FIG. 2 is a cross-sectional view showing a preferred shape of foam layer 19 to ensure it will fit tightly over roller means 11 and to ensure that such layer 19 will rotate with roller means 11 and not independently thereof.

It is within the scope of the present invention to use two or more different resilient materials on roller means 11 to permit optimization of pick-up of different specific chemical residues. The most suitable resilient material for any given residue can be determined by routine experimentation.

It is also within the scope of the, present invention to vary the moisture content of the sorbent layer 19, especially to simulate variations in the moistness of human skin. Moistening of the sorbent layer enhances its similarity to the moist porous skin of adults and young children as to contact transfer.

Referring to the novel method of the instant invention, reference will be directed to the use of the apparatus of the device just described. More particularly, the polyurethane foam layer is applied to the surface such as the floor at a substantial constant pressure. After the requisite surface area has been covered as described below, the thus applied polyurethane foam layer is removed from the roller means by any suitable device that will not contaminate the same, such as a properly cleaned pair of tongs, tweezers or other like device. The foam layer once removed is placed in a suitable extractor such as a Soxhlet extractor with use of an extractant suitable for removing from the foam layer the chemical residue being tested for. Usually these extractants can be hydrocarbons, alcohols, ethers or combinations thereof. The extractant used will be that known to be suitable for the chemical residue. The resultant extract, as is or concentrated as by evaporation, is then tested by suitable means utilized for testing for the particular residue such as analysis by gas chromatography/mass spectrometry (GC/MS) or gas chromatography with electron capture detection (GC/ECD).

The invention will be further described with respect to the examples which follow which are set forth for purposes of illustration only.

EXAMPLES 1-13

A series of pesticides are applied on an aluminum foil test surface in the amount of 100 $\mu g$ each. The efficiency of the apparatus of the instant invention was compared with utilization of an alternative technique using a human hand press test. More particularly, the device shown in FIG. 1 was utilized in which the dimensions of the polyurethane foam layer used, are set forth below.

For purposes of accurate comparison a series of thirteen different pesticides were placed on aluminum foil surfaces and permitted to dry thereon. The percentage of pesticide collected by contact transfer by the device of the invention was compared to pesticide collection by contact transfer by the application of a human hand on each of the pesticide residues.

Four of the spiked pesticides (o-phenylphenol, Propoxur, Diazinon and Carbaryl) were analyzed by gas chromatography/mass spectrometry (GC/MS). Gas chromatography with electron capture detection (GC/ECD) and GC/MS were used as the primary and secondary analytical methods, respectively, for the other spiked pesticides. Since 2-propanol was used to wash the 13 target pesticides (Table I) from the human hand heel in this study, all injection standards for both quantitation methods were prepared in 2-propanol. The internal standard quantitation method was used for GC/MS analyses, while the external standard method was used for GC/ECD analyses.

Aluminum foil preparation involved a new 120 cm $\times$ 30 cm dry acetone-washed aluminum foil strip for each test involving the hand press, instant device, and surface pesticide evaporation loss. A total of 250 $\mu l$ of a 400 $\mu g/ml$ standard solution containing all the pesticides was spiked onto the aluminum foil surface, by using a 250 $\mu l$ syringe to uniformly transfer 25 $\mu l$ of the solution to the center of each of ten 10-cm sections of foil from 1 cm above the surface. Each application took approximately 5 sec. Using this procedure, each spike was observed to dry in a circular disk (radius about 1.3 cm) on the aluminum foil surface in about 75 sec. All the tests involving the instant device, hand press and pesticide evaporative loss from the aluminum foil surface commenced 90 sec. after the last spike was applied and were conducted under the same laboratory conditions (24.3°–25.1° C. at 50.5% relative humidity). This standardized the amount of pesticides left on the aluminum foil after the 90-sec drying period in each test.

Two subjects, one with dry hand and the other with moist hands, performed the hand press contact transfer recovery tests. Each subject washed his hands with soap and water approximately 5 min before each test. For the first hand press recovery test, the subject pressed the heel of the hand (beneath little finger to above wrist) over each dry circular spiked disk on the aluminum foil surface for about 1 sec in a 90° rolling motion (from hand perpendicular to surface to hand flat on surface) at a pressure of about 1 lb/in$^2$. After pressing the same hand heel over the remaining nine spiked spots on the aluminum foil surface, the hand was immediately rinsed by squirting 20 ml of 2-propanol from a squeeze bottle over the hand heel, with the rinsate passing through a collection funnel into a vial. The collection funnel was rinsed with 10 ml of a 2-propanol into the vial. The 30-ml hand rinsate was then concentrated to 1 ml and split for GC/ECD and GC/MS analysis. Each subject performed a second rinse of his hand heel with 2-propanol after the first hand press test. The second rinsate is collected into a different vial, concentrated and analyzed as before. The second rinsing monitored whether any pesticides remained on the hand heel of each subject.

Two different hand motions were also studied. For the second hand press test, all procedures were the same as the first test except the hand heel rested on each pesticide-spiked disk for 5 sec. For the third hand press test, the only difference was to slide the hand heel over each spiked disk.

The instant device used had a removable stainless steel roller. A cylindrical polyurethane foam layer was used with 8.9 cm OD, 5 cm internal opening, 8 cm length and approximately 2.2 cm thickness when inserted on the steel roller. After cleaning by consecutive Soxhlet extraction with acetone and with 6% ether/hexane, this ring was carefully slid onto the stainless steel roller with a dry hexane-washed Teflon ® sheet between the stainless steel roller and ring. The function of the Teflon ® sheet was to ease the ring in sliding on and off the roller.

The tests were designed to simulate the dermal exposure of a one-year old toddler to pesticide residues on a hard surface. The stainless steel roller of the device used in the tests weighed 3.38 kg, which exerted a surface pressure of (3.38 kg$\times$9.8 m/sec$^2$)/(0.080 m$\times$0.057 m)=7300 Pa while rolling over a surface. A crawling, 20-lb child will support his weight with two hands (each approximately 2 in. by 3 in.) and two knees (each approximately 2 in. by 2 in.). The surface pressure when crawling is 20 lb/(2$\times$6 in$^2$+2$\times$4 in$^2$)=1.0 lb/in$^2$=6900 Pa. When walking, the child's weight is supported on two feet (each approximately 2 in.$\times$4 in.), and the surface pressure is 20 lb/(2$\times$8 in$^2$)=1.25 lb/in$^2$=8,600 Pa. Hence the roller used in this study applied the same range of pressure as a one-year child when crawling or walking.

To collect a sample by contact transfer, the roller sampler was pulled once over a spiked aluminum foil strip at a speed of 10 cm/sec. After a single pass, the foam layer was carefully pulled away from the roller using forceps. The forceps were then rinsed with 6% ethyl ether in hexane. The foam layer along with the rinsate was placed in a Soxhlet extractor. The foam layer was then extracted with 6% ethyl ether in hexane for 18 hours and the final extract concentrated to 2 ml for both GC/MS and GC/ECD analysis.

The pesticides in hexane were spiked on the aluminum foil surface and the solvent evaporated to leave pesticide residue spots. Experiments were performed to evaluate the loss of pesticides due to evaporation during the 90-sec drying time.

Ten 4 cm×4 cm dry acetone-cleaned squares of aluminum foil were placed on a 120 cm×30 cm aluminum foil strip and each aluminum square spiked from 1 cm above surface, with 25 μl of a 400 μg/ml standard solution containing all the compounds in Table I below, allowing 5 sec to apply each spike. The ten squares were collected in a Soxhlet extractor 90 sec after application of the last spike and extracted with 6% ethyl ether in hexane for 18 hours. The extract was concentrated to 2 ml and split equally for GC/ECD and GC/MS analysis. This pesticide evaporative loss experiment was performed three times in the same manner and the results set forth in Table I.

Two clean polyurethane foam layers were each spiked with 250 μl of the 400 μg/ml standard solution in hexane containing each compound in Table I. Each layer was then Soxhlet extracted separately with 6% ethyl ether in hexane for 18 hours and each extract concentrated to 2 ml and split equally for GC/ECD and GC/MS analysis. This was done to determine the extraction efficiency of the pesticides from the layers.

The results of all these tests are set forth in Tables I, II and III below.

TABLE I

Pesticide Evaporative Loss From Aluminum Foil Surface[a]

| Spiked Pesticides | Percent Recovery | | | |
|---|---|---|---|---|
| | Test 1 | Test 2 | Test 3 | Mean Recovery |
| o-Phenylphenol | 61 | 101 | 101 | 88 |
| Propoxur | 85 | 136 | 130 | 117 |
| Diazinon | 82 | 115 | 113 | 103 |
| Carbaryl | 78 | 217 | 53 | 116 |
| Heptachlor | 83 | 98 | 104 | 95 |
| Aldrin | 80 | 98 | 104 | 94 |
| Chlorpyrifos | 82 | 102 | 107 | 97 |
| γ-Chlordane | 86 | 103 | 108 | 99 |
| α-Chlordane | 87 | 103 | 108 | 99 |
| p,p'-DDE | 87 | 105 | 111 | 101 |
| Dieldrin | 87 | 104 | 109 | 100 |
| Methoxychlor | 102 | 105 | 113 | 107 |
| Permethrin | 111 | 106 | 110 | 109 |

[a]Last spiked residue spot allowed to dry for 90 seconds before spiked foil squares were placed in Soxhlet extractor.

TABLE II

Extraction Efficiency of Pesticide From Foam Ring

| Spiked Pesticides | Spiked Amount (μg) | Percent Recovery | | |
|---|---|---|---|---|
| | | Test 1 | Test 2 | Mean Recovery |
| o-Phenylphenol | 100 | 70 | 95 | 83 |
| Propoxur | 100 | 89 | 162 | 126 |
| Diazinon | 100 | 90 | 127 | 94 |
| Carbaryl | 100 | 84 | 144 | 114 |
| Heptachlor | 100 | 92 | 99 | 96 |
| Aldrin | 100 | 88 | 99 | 94 |
| Chlorpyrifos | 100 | 90 | 101 | 96 |
| γ-Chlordane | 100 | 94 | 100 | 97 |
| α-Chlordane | 100 | 95 | 101 | 98 |
| p,p'-DDE | 100 | 96 | 103 | 100 |
| Dieldrin | 100 | 96 | 102 | 99 |
| Methoxychlor | 100 | 102 | 105 | 104 |
| Permethrin | 100 | 108 | 103 | 106 |

TABLE III

Efficiency of Isopropanol Rinse of Hand Heel After Hand Heel Press

| Spiked Pesticides | Percent Rinse Efficiency[a] | |
|---|---|---|
| | Subject 1 | Subject 2 |
| o-Phenylphenol | 88 | 100 |
| Propoxur | 79 | 99 |
| Diazinon | 90 | 98 |
| Carbaryl | 82 | 99 |
| Heptachlor | 96 | 99 |
| Aldrin | 97 | 99 |
| Chlorpyrifos | 97 | 99 |
| γ-Chlordane | 98 | 99 |
| α-Chlordane | 98 | 99 |
| p,p'-DDE | 98 | 100 |
| Dieldrin | 98 | 99 |
| Methoxychlor | 97 | 99 |
| Permethrin | 98 | 99 |

[a]Efficiency (%) = $\frac{\text{First Rinse Recovery}}{\text{First Rinse Recovery + Second Rinse Recovery}}$ The analytical results of the pesticide evaporative loss shown thereon is almost no loss of each pesticide from the aluminum foil surface 90 sec after the last spiking. Therefore, no correction was made for the evaporataive loss of any pesticide from the aluminum foil surface. Table II demonstrates good extraction recovery for all the pesticides from the foam layer. Thus no correction efficiency was made.

After the first hand press test, each human subject rinsed his hand heel twice. For each pesticide, the ratio of the amount recovered in the first rinsing divided by the corresponding total amount recovered in both rinsings is shown in Table III. It is clear that almost all pesticides are recovered in the first rinsing.

The three replicate results of the roller polyurethane foam contact transfer recoveries of the pesticides spiked on an aluminum foil strip after pulling the foam layer once over the spots are shown in Table IV. In general, the three recoveries of each pesticide are consistent in the replicate tests. The mean recovery of each pesticide is between 5 to 9% with a relative standard deviation less than 32%. An extra test was performed in which the roller jammed after rolling over seven spiked spots and slid over the remaining three spots. Table IV below shows the recoveries were at least double in this test. Therefore, sliding the foam layer instead of just rolling over the pesticide spiked spots will increase the pesticide contact transfer recovery substantially.

TABLE IV

Polyurethane Foam Layer Pesticide Contact Transfer Recovery[a]

| Spiked Pesticides | Percent Recovery[b] | | | | | Recovery from Layer Slide Test[c] |
|---|---|---|---|---|---|---|
| | Test 1 | Test 2 | Test 3 | Recovery Mean | Std Dev | |
| o-Phenylphenol | 5.2 | 7.8 | 10 | 7.7 | 2.4 | 16 |
| Propoxur | 5.9 | 9.7 | 7.9 | 7.8 | 1.9 | 29 |
| Diazinon | 5.4 | 6.9 | 7.2 | 6.5 | 1.0 | 20 |
| Carbaryl | 3.8 | 5.9 | 6.4 | 5.4 | 1.4 | 33 |
| Heptachlor | 7.0 | 8.0 | 8.5 | 7.8 | 0.8 | 18 |
| Aldrin | 7.6 | 7.6 | 8.5 | 7.9 | 0.5 | 18 |
| Chlorpyrifos | 5.5 | 6.9 | 8.8 | 7.1 | 1.7 | 17 |
| γ-Chlordane | 7.9 | 6.8 | 8.7 | 7.8 | 1.0 | 18 |
| α-Chlordane | 7.6 | 6.9 | 8.4 | 7.6 | 0.8 | 18 |
| p,p'-DDE | 8.0 | 7.5 | 9.4 | 8.3 | 1.0 | 21 |
| Dieldrin | 6.6 | 6.6 | 8.4 | 7.2 | 1.0 | 18 |
| Methoxychlor | 11 | 6.6 | 8.9 | 8.8 | 2.2 | 18 |

TABLE IV-continued

Polyurethane Foam Layer Pesticide Contact Transfer Recovery[a]

| Spiked Pesticides | Percent Recovery[b] | | | | | Recovery from Layer Slide Test[c] |
|---|---|---|---|---|---|---|
| | Test 1 | Test 2 | Test 3 | Recovery Mean | Std Dev | |
| Permethrin | 7.7 | 6.7 | 9.2 | 7.9 | 1.3 | 18 |

[a]The roller exerted a pressure of 7300 Pa through the foam layer when rolling over the foil surface.
[b]The layer rolled over 10 spots (total 100 μg for each pesticide) at 10 cm apart at a speed of 10 cm per second.
[c]The roller accidentally jammed after rolling over 7 of the 10 residue spots so that the foam layer slid over the remaining 3 spots.

The results of hand heel press contact transfer recovery of pesticides by both dry and moist hands using three different hand motion over the ten dry pesticide residue spots are shown in Tables V and VI, respectively. The mean contact transfer pesticide recoveries were between 5 to 16%, with larger variations than recoveries by the instant device. This larger variation may be due to the different types of hand heel presses applied. The pesticide recoveries of the dry and moist hand heel roll presses with 1 sec duration have similar values. The pesticide recovery of the dry hand press for 5 sec has similar recovery as that of the 1 sec roll press, but the dry hand slide collects more of the less volatile pesticides than either of the other dry hand press motions. The moist hand press for 5 sec collects more of the less volatile pesticides than the 1 sec roll press by the same hand. However, the moist hand has more friction while sliding over residues on the aluminum foil surface which causes the moist hand to skip. The moist hand skipping may cause the lower pesticide recovery than the dry hand obtained in the hand press slide. These data suggest that the hand heel roll is more reproducible between subjects than other hand press motions.

TABLE V

Hand Heel Press Contact Transfer Recovery of Pesticides By Dry Hand Using Three Hand Motions Over Ten Dried Spiked Pesticide Spots

| Spiked Pesticides | Percent Recovery by Hand Heel Motion[a] | | | | |
|---|---|---|---|---|---|
| | 1s Heel Press | 5s Heel Press | Heel Slide | Subject 1 | |
| | | | | Mean | Std Dev |
| o-Phenylphenol | 8.4 | 13 | 9.7 | 10.4 | 2.4 |
| Propoxur | 5.4 | 4.2 | 6.5 | 5.4 | 1.2 |
| Diazinon | 6.4 | 5.6 | 7.0 | 6.3 | 0.7 |
| Carbaryl | 9.3 | 7.7 | 11 | 9.3 | 1.7 |
| Heptachlor | 9.5 | 9.0 | 8.6 | 9.0 | 0.5 |
| Aldrin | 9.5 | 9.3 | 10.0 | 9.6 | 0.4 |
| Chlorpyrifos | 7.7 | 6.4 | 9.1 | 7.7 | 1.4 |
| γ-Chlordane | 8.6 | 6.6 | 9.8 | 8.3 | 1.6 |
| α-Chlordane | 8.6 | 6.8 | 11 | 8.8 | 2.1 |
| p,p'-DDE | 8.6 | 7.2 | 12 | 9.3 | 2.5 |
| Dieldrin | 8.8 | 6.7 | 11 | 8.8 | 2.2 |
| Methoxychlor | 6.7 | 8.5 | 16 | 10 | 4.9 |
| Permethrin | 6.4 | 7.4 | 20 | 11.2 | 7.6 |

[a]All motions at hand heel pressure on foil of about 1 lb/sq in. (7000 Pa).

TABLE VI

Hand Heel Press Contact Transfer Recovery of Pesticide By Moist Hand Using Three Hand Motions over Ten Dried Spiked Pesticide Spots

| Spiked Pesticides | Percent Recovery by Hand Heel Motion[a] | | | | |
|---|---|---|---|---|---|
| | 1s Heel Press | 5s Heel Press | Heel Slide[b] | Subject 2 | |
| | | | | Mean | Std Dev |
| o-Phenylphenol | 10.3 | 8.0 | 6.3 | 8.2 | 2.0 |
| Propoxur | 7.2 | 5.4 | 3.9 | 5.5 | 1.7 |
| Diazinon | 9.8 | 9.8 | 4.9 | 8.2 | 2.8 |
| Carbaryl | 9.6 | 7.2 | 4.6 | 7.1 | 2.5 |
| Heptachlor | 10 | 13 | 5.6 | 9.5 | 3.7 |
| Aldrin | 9.9 | 14 | 6.8 | 10.2 | 3.6 |
| Chlorpyrifos | 8.9 | 11 | 6.1 | 8.7 | 2.5 |
| γ-Chlordane | 9.3 | 13 | 6.7 | 9.7 | 3.2 |
| α-Chlordane | 9.3 | 13 | 7.4 | 9.9 | 2.8 |
| p,p'-DDE | 9.2 | 14 | 8.3 | 10.5 | 3.1 |
| Dieldrin | 9.4 | 13 | 7.3 | 9.9 | 2.9 |
| Methoxychlor | 8.5 | 22 | 8.5 | 13.0 | 7.8 |
| Permethrin | 7.8 | 22 | 17 | 15.6 | 7.2 |

[a]All motions at hand heel pressure on foil of about 1 lb/sq in. (7000 Pa).
[b]Hand heel observed to skip while sliding over residue spots on aluminum foil.

The null hypothesis of no difference in mean contact transfer recovery between the polyurethane foam layer and the hand press was evaluated against the two-sided alternative for each pesticide by the two-sample t-test at the 0.05 significance level. All hand press recoveries of both subjects were combined since mean dermal recovery did not differ significantly between the subjects for any spike pesticide. The results shown in Table VII indicate there is no statistically significant difference in mean contact transfer recovery between the polyurethane foam layer and the hand press for any of the 13 spiked pesticides.

TABLE VII

Comparison of Mean Contact Transfer Recovery Pesticide Residues by Roller and Heel Press

| Spiked Pesticides | Mean Contact Transfer Recovery of Residue from Aluminum Foil, Percent | | Statistically Significant Difference?[b] (p-value) |
|---|---|---|---|
| | Polyurethane Foam Layer | Hand Press[a] | |
| o-Phenylphenol | 7.7 | 9.3 | No |
| Propoxur | 7.8 | 5.4 | No (p = 0.055) |
| Diazinon | 6.5 | 7.2 | No |
| Carbaryl | 5.4 | 8.2 | No (p = 0.08) |
| Heptachlor | 7.8 | 9.3 | No |
| Aldrin | 7.9 | 9.9 | No |
| Chlorpyrifos | 7.1 | 8.2 | No |
| γ-Chlordane | 7.8 | 9.0 | No |
| α-Chlordane | 7.6 | 9.4 | No |
| p,p'-DDE | 8.3 | 9.9 | No |
| Dieldrin | 7.2 | 9.4 | No |
| Methoxychlor | 8.8 | 11.7 | No |
| Permethrin | 7.9 | 13.4 | No |

[a]For both subjects, since there was no statistically significant difference in mean dermal contact recovery between subjects for any spiked pesticide.
[b]Two sample two-sided t-test of difference in mean recovery at α = 0.05. p-values of borderline significant differences in parentheses.

This finding suggests that the instant device and method are an ideal dermal exposure sampling apparatus and technique.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. Propellable apparatus for use in sampling for the contact transfer of chemical residue on a surface possibly containing a chemical residue so as to determine human's dermal exposure to said chemical residue by coming into dermal contact with said surface, comprising frame means comprising shoulder means and leg means pivotably attached at one end thereof to said shoulder means, said shoulder means mounted on movable supports, roller means rotably attached to said leg means at a second end thereof, propelling means attached to said shoulder means to propel said apparatus, and a cylindrical layer of a resilient material, which has chemical residue contact transfer absorption properties similar to human skin removably mounted on said roller means, whereby pressure, applied to said shoulder means is transmitted to said movable supports and not said roller means and the pressure of said roller means on said surface is based on the weight of said roller means and is maintained constant regardless of the pressure applied to said shoulder means.

2. The apparatus of claim 1 wherein said cylindrical layer is a polyurethane foam.

3. The apparatus of claim 2 including an absorptive outer layer covering at least a portion of the exterior of said resilient layer.

* * * * *

UNITED STATES PATENT AND TRADEMARK OFFICE
CERTIFICATE OF CORRECTION

PATENT NO. : 5,243,865
DATED : September 14, 1993
INVENTOR(S) : Hsu, et al

It is certified that error appears in the above-indentified patent and that said Letters Patent is hereby corrected as shown below:

On the Title Page, Item [75], correct the inventor's name to be --Jong-Pyng--.

Signed and Sealed this

Thirty-first Day of May, 1994

Attest:

BRUCE LEHMAN

*Attesting Officer*      *Commissioner of Patents and Trademarks*